United States Patent [19]
Bierschenk et al.

[11] 4,195,190
[45] Mar. 25, 1980

[54] PREPARATION OF ETHYLENE GLYCOL

[75] Inventors: Thomas R. Bierschenk, Corpus Christi; Rowland Pettit, Austin; Donald R. Nielsen, Corpus Christi, all of Tex.

[73] Assignee: PPG Industries, Inc., Pittsburgh, Pa.

[21] Appl. No.: 892,791

[22] Filed: Apr. 3, 1978

[51] Int. Cl.$^2$ .................. C07C 29/02; C07C 31/20
[52] U.S. Cl. .................................................. 568/860
[58] Field of Search ................................. 568/860

[56] References Cited
U.S. PATENT DOCUMENTS

| | | | |
|---|---|---|---|
| 1,982,545 | 11/1934 | Skarblom | 568/860 |
| 2,780,528 | 2/1957 | Fossan et al. | 568/860 |
| 3,479,395 | 11/1969 | Huguet | 568/860 |
| 3,928,474 | 12/1975 | Witheford | 568/860 |
| 4,045,500 | 8/1977 | Onsager et al. | 568/860 |

*Primary Examiner*—Joseph E. Evans
*Attorney, Agent, or Firm*—Edward J. Whitfield

[57] ABSTRACT

Ethylene glycol is produced by the liquid phase reaction of ethylene, oxygen and water in the presence of a catalyst comprising iodine or an iodine-containing compound and bromine or a bromine-containing compound.

4 Claims, No Drawings

PREPARATION OF ETHYLENE GLYCOL

BACKGROUND OF THE INVENTION

Ethylene glycol is used extensively in the preparation of antifreeze compositions and may be prepared by various known processes. One such process, described in U.S. Pat. No. 1,982,545, involves the iodine catalyzed liquid phase oxidation of ethylene. Variations on this process are described, for example, in U.S. Pat. Nos. 3,928,474 and 4,045,500.

Generally, the said iodine catalyzed liquid phase reaction may be represented as follows:

$$CH_2=CH_2 + I_2 \rightarrow ICH_2-CH_2I \quad (1)$$

$$ICH_2-CH_2I + H_2O \rightarrow HOCH_2-CH_2I + HI \quad (2)$$

$$HOCH_2-CH_2I + H_2O \rightarrow OHCH_2-CH_2OH + HI \quad (3)$$

$$2HI + \tfrac{1}{2}O_2 \rightarrow H_2 + I_2 \quad (4)$$

The net reaction may be represented thus:

$$CH_2=CH_2 + \tfrac{1}{2}O_2 + H_2O \rightarrow HOCH_2-CH_2OH.$$

The iodination of ethylene (1), the primary hydrolysis of ethylene iodide (2), and the oxidation of hydriodic acid (4) all proceed rapidly compared with the hydrolysis of ethylene iodohydrin (3). Since this latter reaction is the rate-limiting step of the process, it is desirable to devise means for accelerating the same. It has been found that improved yields of ethylene glycol are obtained when the said liquid phase reaction of ethylene, oxygen, and water is conducted in the presence of a mixed iodine/bromine catalyst, as compared with the same reaction catalyzed by iodine alone.

SUMMARY OF THE INVENTION

Ethylene glycol is produced by a process comprising reacting in a liquid medium ethylene, oxygen, and water in the presence of a catalytic amount of iodine or an iodine-containing compound and bromine or a bromine-containing compound.

DESCRIPTION OF THE INVENTION

In accordance with a preferred embodiment of this invention, ethylene, oxygen, and water are brought together in an autoclave reactor in the presence of a catalytic amount of iodine or an iodine-containing compound and bromine or a bromine-containing compound.

Reactant ratios may vary over a wide range. For example, the molar ratio of ethylene to oxygen may range from 10:1 to 1:10 and the molar ratio of ethylene to water may vary from 0.1:1 to 10:1. Although satisfactory results typically obtain using stoichiometric quantities of ethylene and oxygen, it has been found that the yield of ethylene glycol is improved somewhat at an ethylene:oxygen molar ratio of about 2:3.

The reaction is typically conducted at elevated temperatures of from about 50° C. to about 175° C., preferably from about 125° C. to 165° C. with an optimum reaction temperature in the range of 145° C. to 155° C. The reaction is conducted at an elevated pressure sufficient to maintain the liquid phase and preferably at least about 175 psig. Although lower pressure may be used, it has been found that the yield of ethylene glycol is somewhat reduced. Although a pressure as high as about 1000 psig may be used, satisfactory results obtain in the range of about 175 psig to about 500 psig, and preferably between about 200 psig and 300 psig.

Residence time in the reactor is typically in the range of a few minutes to several hours, usually from about 30 minutes to about 5 hours. At the completion of the reaction, the liquid reaction product is withdrawn from the reactor and ethylene glycol is recovered therefrom in known manner by, for example, vacuum distillation.

Iodine or an iodine-containing compound is present in the liquid reaction mixture in amounts ranging from about 0.1 percent to about 20 percent, preferably from about 2.0 percent to about 10 percent, expressed as HI, based on the weight of liquid, with an optimum concentration of between about 5 percent to 7 percent by weight expressed as HI. The iodine-containing compound may be hydriodic acid or a metal iodide or an organic iodine compound which hydrolyze to form HI under reaction conditions, such as, for example, ferric iodide, ferrous iodide, chromous iodide, chromic iodide, zinc iodide, ethylene diiodide, iodoethanol and the like. Hydriodic acid is particularly preferred.

Bromine or a bromine-containing compound is present in the liquid reaction mixture in amounts ranging up to about one mole of bromine expressed as HBr per mole of HI-iodine. The bromine-containing compound may be hydrobromic acid or a metal bromide or an organic bromine compound which hydrolyze to form HBr under reaction conditions, such as, for example, ferric bromide, ferrous bromide, chromic bromide, chromous bromide, ethylene dibromide, bromoethanol and the like. Hydrobromic acid is particularly preferred. Although precise limits of HBr concentration for the operability of the invention have not been formulated, it is believed that at a molar concentration of HBr:HI in excess of 1:1, the advantage afforded by the practice of the invention, i.e., increased yield of ethylene glycol, would be considerably diminished. For example, at a HBr:HI molar ratio of 1:1, the yield of ethylene glycol was observed to be about 7 percent higher than a reaction catalyzed by iodine alone, and at a HBr:HI molar ratio of 0.9:1, about a 20 percent higher yield of ethylene glycol was obtained, the molar concentration of HI and reaction conditions being the same in all cases.

It is contemplated, therefore, that in the practice of this invention, a molar ratio of HBr:HI in the range of from about 0.01:1, to about 1:1 would result in measurably improved yields of ethylene glycol with the most beneficial results obtaining at a molar ratio of HBR:HI in the range of from about 0.1:1 to 0.9:1.

That improved yields of ethylene glycol are obtained by the iodine-bromine catalyzed liquid phase oxidation of ethylene according to the invention as compared with the liquid phase oxidation of ethylene catalyzed by iodine alone, is indeed surprising and unexpected especially in view of the observation that bromine alone was found ineffective as a catalyst under identical reaction conditions.

The invention is further illustrated but is not intended to be limited by the following examples.

EXAMPLE 1

The experimental apparatus used was a Hastelloy-C, 1-liter capacity, Magnedrive Autoclave available from Autoclave Engineers, Inc. Stainless steel was used in the construction of the gas feed and vent system. The autoclave was charged with 400 grams of 5.1 weight percent aqueous hydriodic acid (HI) solution via a filling port. The autoclave was pressurized to about 275 psig with nitrogen to check for leaks and then swept with ethylene at a rate of about 1 liter per minute for about 10 minutes. The autoclave was then pressurized to about 100 psig with a 1:1 mixture of ethylene and oxygen and brought up to operating temperature. When the desired reaction temperature, i.e., 150° C., was reached, the gas flows were adjusted to 0.6 liter pr minute each of oxygen and ethylene and the vent was opened to maintain the desired reaction pressure, i.e., 219 psig. After a reaction time of 3 hours, the autoclave was cooled and swept with nitrogen for about 30 minutes at a rate of 1 liter per minute at the reaction pressure of 219 psig. The product liquor was allowed to stand overnight in the autoclave under a nitrogen atmosphere, after which the autoclave was opened and the product liquor was siphoned out and analyzed for ethylene glycol content. a yield of 0.74 moles of monoethylene glycol was obtained.

EXAMPLE 2

The procedure described in Example 1 was followed except that the autoclave was charged with 400 grams of a 3.4 weight percent aqueous hydrobromic acid (HBr) solution. Under identical reaction conditions a yield of 0.036 mole of monethylene glycol was obtained.

EXAMPLE 3

The procedure described in Example 1 was followed except that the autoclave was charged with 400 grams of an aqueous solution containing 5.1 weight percent HI and 2.9 weight percent HBr (0.9:1 molar ratio HBr:HI). Under identical reaction conditions a yield of 1.49 moles of monoethylene glycol was obtained.

From the foregoing it is seen that the iodine-bromine catalyzed liquid phase oxidation of ethylene according to the invention (Example 3) resulted in a two-fold increase in ethylene glycol yield as compared with the iodine catalyzed system (Example 1) whereas the bromine catalyzed system (Example 2) yield a comparatively negligible amount of ethylene glycol.

Although the invention has been described with specific references to and specific embodiments thereof, it is to be understood that it is not intended to be so limited since changes and alterations therein may be made which are within the full and intended scope of this invention as defined by the appended claims.

We claim:

1. In a process for preparing ethylene glycol wherein ethylene, oxygen and water are reacted in the presence of a catalyst at a moderately elevated temperature under a pressure sufficient to maintain the liquid phase and for a time sufficient to effect the desired degree of conversion, the improvement wherein said catalyst consists of an iodine source which is iodine or an iodine compound and a bromine source which is bromine or a bromine compound wherein the molar ratio of bromine, expressed as HBr, to iodine, expressed as HI, is not more than about 1:1.

2. The improvement of claim 1 wherein the iodine source is iodine, hydriodic acid, a metal iodide, or an organic iodine compound and the bromine source is bromine, hydrobromic acid, a metal bromide, or an organic bromine compound.

3. The improvement of claim 2 wherein the iodine source is present in sufficient quantity such that the HI concentration is from about 0.1 percent to 20 percent by weight based on the weight of liquid phase and the bromine source is present in sufficient quantity such that the molar ratio of HBr:HI is from about 0.01:1 to about 1:1.

4. The improvement of claim 3 wherein the molar ratio of HBr:HI is from about 0.1:1 to 0.9:1.

* * * * *